United States Patent
Yoshikawa et al.

(10) Patent No.: US 9,427,202 B2
(45) Date of Patent: Aug. 30, 2016

(54) ARITHMETIC PROCESSOR AND BONE DENSITY MEASURING DEVICE

(71) Applicant: FUJIFILM Corporation, Tokyo (JP)

(72) Inventors: Kenji Yoshikawa, Kanagawa-ken (JP); Takuma Okuno, Kanagawa-ken (JP); Tsuyoshi Kamada, Hamamatsu (JP)

(73) Assignee: FUJIFILM Corporation, Tokyo (JP)

( * ) Notice: Subject to any disclaimer, the term of this patent is extended or adjusted under 35 U.S.C. 154(b) by 250 days.

(21) Appl. No.: 14/323,134

(22) Filed: Jul. 3, 2014

(65) Prior Publication Data

US 2016/0000394 A1   Jan. 7, 2016

(51) Int. Cl.
| | |
|---|---|
| *G01N 23/06* | (2006.01) |
| *A61B 6/00* | (2006.01) |
| *G01N 9/24* | (2006.01) |
| *G01N 23/00* | (2006.01) |

(52) U.S. Cl.
CPC .............. *A61B 6/505* (2013.01); *A61B 6/5217* (2013.01); *G01N 9/24* (2013.01); *G01N 23/00* (2013.01); *A61B 6/54* (2013.01); *A61B 6/582* (2013.01)

(58) Field of Classification Search
CPC ........ A61B 6/52; A61B 6/505; A61B 6/583; A61B 6/582; A61B 6/585; A61B 6/482; A61B 6/4233; A61B 6/58; G01N 9/24; G01N 2223/303; G01N 2223/3035; G06T 7/0012; G06T 2207/10116; G01T 7/005
See application file for complete search history.

(56) References Cited

U.S. PATENT DOCUMENTS

| | | | | |
|---|---|---|---|---|
| 6,320,931 B1 * | 11/2001 | Arnold | ................. | A61B 6/4035 378/54 |
| 6,438,201 B1 * | 8/2002 | Mazess | .................. | A61B 6/405 378/108 |
| 6,904,123 B2 * | 6/2005 | Lang | ...................... | A61B 6/508 378/54 |

FOREIGN PATENT DOCUMENTS

| | | |
|---|---|---|
| JP | 2793502 B2 | 9/1998 |
| JP | 2006-334046 A | 12/2006 |

* cited by examiner

*Primary Examiner* — Hoon Song
(74) *Attorney, Agent, or Firm* — McGinn IP Law Group, PLLC

(57) ABSTRACT

An arithmetic processor for measuring bone density using a correspondence relationship between a luminance value of transmitted radiation and a thickness of a reference material is provided. The luminance value is obtained by applying radiation, which is emitted from a radiation source upon application of a tube voltage to the radiation source, to the reference material having different thicknesses and detecting the radiation transmitted through the reference material. The arithmetic processor includes: a generating unit that generates, based on the detected luminance value, a luminance profile representing the correspondence relationship; a normalizing unit that generates a normalized profile by normalizing the luminance profile based on a maximum value and a minimum value in the luminance profile; and a determining unit that determines whether or not each luminance value corresponding to each thickness in the normalized profile is within a range defined in advance by the tube voltage and each thickness.

6 Claims, 6 Drawing Sheets

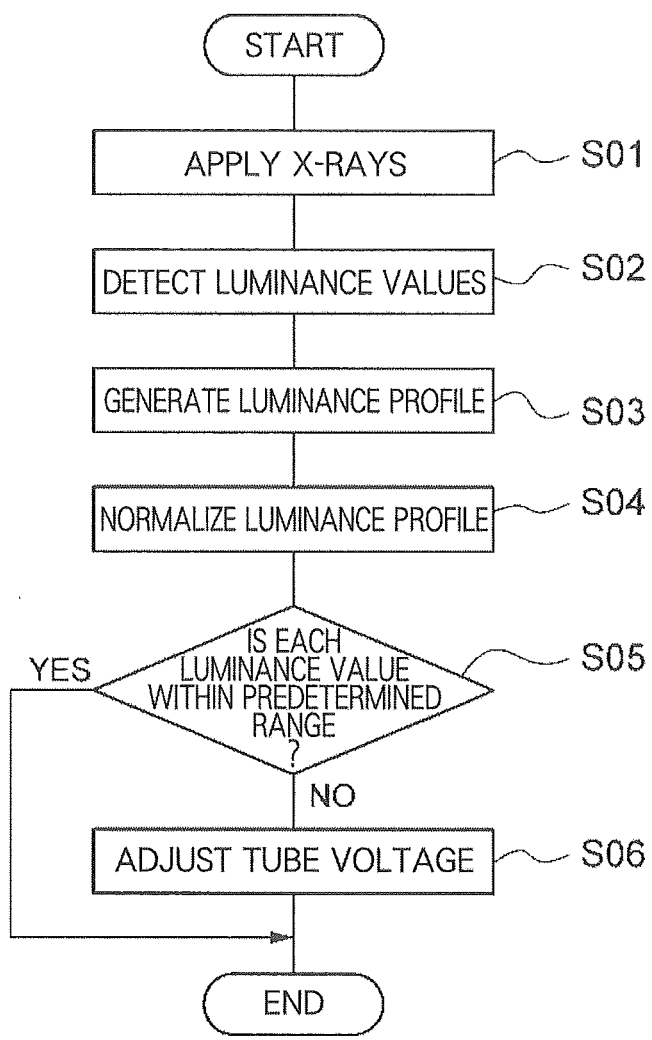

ARITHMETIC PROCESSOR AND BONE DENSITY MEASURING DEVICE

CROSS-REFERENCE TO RELATED APPLICATIONS

Japanese Patent Application No. 2011-286407 filed Dec. 27, 2011, which corresponds to the present application, is hereby expressly incorporated by reference, in its entirety, into the present application.

BACKGROUND OF THE INVENTION

1. Field of the Invention

The present invention relates to an arithmetic processor for measuring bone density using a correspondence relationship between a luminance value of transmitted radiation and a thickness of a reference material, the luminance value being obtained by applying radiation, which is emitted from a radiation source upon application of a tube voltage to the radiation source, to the reference material having different thicknesses and detecting the radiation transmitted through the reference material, and a bone density measuring device provided with the arithmetic processor.

2. Description of the Related Art

Conventionally, the MD method, the DIP method, etc., for example, are known as methods for measuring bone mineral content to check growth status, or the like, of human bones. In the MD method taught in Japanese Unexamined Patent Publication No. 2006-334046 (hereinafter, Patent Document 1), an aluminum step wedge is imaged under the same imaging conditions as those used for X-ray imaging of a body site to be measured of the subject, and the result of the imaging is used to perform correction for variation among photoelectric conversion elements forming the sensor and correction for aging of the sensor element. The imaging conditions can be inputted via an imaging condition input unit, and the inputted imaging conditions are displayed on an imaging condition display area.

In the DIP method taught in Japanese Patent No. 2793502 (hereinafter, Patent Document 2), an aluminum scale and the palms of the subject are placed on an X-ray film and are imaged using an X-ray with a tube voltage of 50 kV being inputted and set. In imaging conditions in the DIP method, usually, a tube voltage of 50 kV, which provides the best correlation between the bone (hydroxyapatite) and the aluminum, is set as a recommended tube voltage.

SUMMARY OF THE INVENTION

With the MD method taught in Patent Document 1, however, although correction of the detection system, such as the correction for variation among photoelectric conversion elements forming the sensor and the correction for aging of the sensor element, is performed, correction of the output system, such as correction for a difference between the tube voltage of the X-ray displayed on the imaging condition display area (which will hereinafter be referred to as "displayed tube voltage") and the tube voltage of the actually applied X-ray (which will hereinafter be referred to as "effective tube voltage"), is not performed. Similarly, correction of the output system is not performed in the DIP method taught in Patent Document 2.

X-ray generators installed at a hospital or a clinic may have a difference between the displayed tube voltage and the effective tube voltage and the effective tube voltage may not be equivalent to the displayed tube voltage, due to aging, or the like, for example. Further, since the height of the X-ray light source may vary depending on the device and performance of the X-ray detector may vary depending on the device, digital values (densities) of detected luminance values may largely vary depending on the device.

FIG. 1 shows a graph where digital values (densities) of luminance values, which are obtained by applying X-rays (with five different effective tube voltages of 40, 46, 50, 55 and 60 kV) to an aluminum slope (which is a sloped aluminum wedge) and inverting intensities of each X-rays transmitted through the aluminum slope, are plotted along the ordinate, and thicknesses of the aluminum slope (positions on the aluminum) are plotted along the abscissa. Even when the displayed tube voltage is 50 kV, if the effective tube voltage is decreased to 46 kV due to aging, or the like, for example, digital values are largely changed, as shown in FIG. 1, and it is impossible to obtain digital values (densities) of correct luminance values.

In order to determine whether or not the effective tube voltage is appropriate relative to the displayed tube voltage, it is necessary to measure the effective tube voltage. However, a tube voltmeter, which is known as an instrument for measuring the effective tube voltage, is very expensive and is therefore difficult to be introduced.

In view of the above-described circumstances, the present invention is directed to providing an arithmetic processor and a bone density measuring device that allow evaluating whether or not the tube voltage of actually applied X-rays is appropriate relative to a desired tube voltage, without using a tube voltmeter.

In order to address the above-described problem, an arithmetic processor according to the invention is an arithmetic processor for measuring bone density using a correspondence relationship between a luminance value of transmitted radiation and a thickness of a reference material, the luminance value being obtained by applying radiation, which is emitted from a radiation source upon application of a tube voltage to the radiation source, to the reference material having different thicknesses and detecting the radiation transmitted through the reference material, the arithmetic processor comprising: a generating unit that performs an operation to generate, based on the detected luminance value, a luminance profile representing the correspondence relationship; a normalizing unit that performs an operation to generate a normalized profile by normalizing the luminance profile based on a maximum value and a minimum value in the generated luminance profile; and a determining unit that performs an operation to determine whether or not each luminance value corresponding to each of the different thicknesses in the normalized profile is within a range defined in advance by the tube voltage and each thickness.

According to the arithmetic processor of the invention, first, a luminance profile is generated based on luminance values obtained by applying radiation to the reference material having different thicknesses, and then a normalized profile is generated based on the maximum value and the minimum value in the luminance profile. Then, whether or not each luminance value corresponding to each of the different thicknesses in the normalized profile is within the range defined by the tube voltage and each thickness of the reference material is determined.

As described above, in place of using a tube voltmeter, luminance values obtained by applying radiation to the reference material having different thicknesses are used to determine whether or not each luminance value corresponding to the tube voltage of actually applied radiation is within a range corresponding to a desired tube voltage. As a result, whether or not the tube voltage of the actually applied radiation is appropriate relative to the desired tube voltage can be evaluated without using a tube voltmeter.

A bone density measuring device according to the invention comprises: the above-described arithmetic processor; a carrying unit on which a subject's bone to be exposed to the radiation emitted upon application of the tube voltage is placed; and a detecting unit that detects radiation transmitted through the subject's bone and the reference material.

According to the bone density measuring device of the invention, radiation transmitted through the subject's bone and the reference material can be detected with placing the subject's bone, which is exposed to the radiation emitted upon application of the tube voltage, on the carrying unit.

In the bone density measuring device of the invention, it is desirable that the different thicknesses in the normalized profile be within the range from 30 mm to 130 mm.

In the case where the different thicknesses in the normalized profile are within the range from 30 mm to 130 mm, whether or not the tube voltage of actually applied radiation is appropriate relative to a desired tube voltage can be evaluated more accurately.

In the bone density measuring device of the invention, the generating unit may perform the operation to generate the luminance profile by using an average value of luminances detected for portions having the same thickness of the reference material as the luminance value corresponding to the thickness.

In this aspect, the luminance profile is generated using an average value of luminances detected for portions having the same thickness of the reference material as the luminance value corresponding to the thickness. By using an average value of luminances detected for portions having the same thickness of the reference material as the luminance value corresponding to the thickness, a more accurate luminance profile can be generated.

According to the invention, an arithmetic processor and a bone density measuring device that allow evaluating whether or not the tube voltage of actually applied X-rays is appropriate relative to a desired tube voltage without using a tube voltmeter are provided.

BRIEF DESCRIPTION OF THE DRAWINGS

FIG. 9 is a flow chart for explaining key steps in a bone density measuring method performed by one embodiment of the bone density measuring device of the invention.

DESCRIPTION OF THE PREFERRED EMBODIMENTS

Hereinafter, a preferred embodiment of the present invention will be described in detail with reference to the appended drawings. In descriptions of the drawings, identical or equivalent elements are denoted by the same reference symbols, and explanations thereof are not repeated.

(1) Outline of Embodiment

Figure 1:
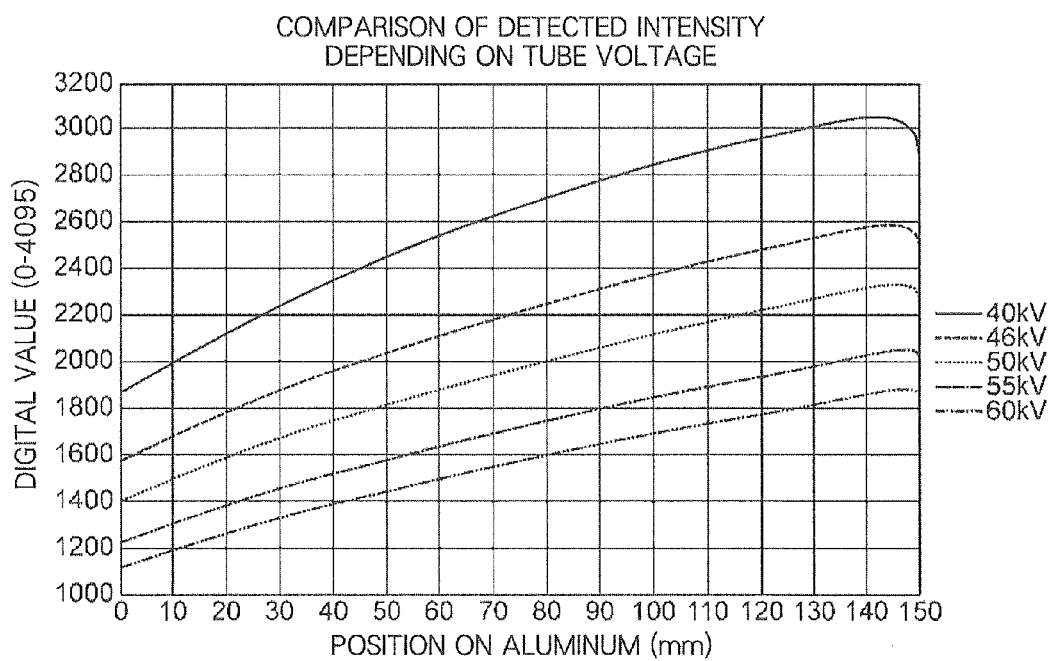
FIG. 1 is a graph where luminance values obtained by inverting intensities of X-rays transmitted through an aluminum slope are plotted along the ordinate, and thicknesses of the aluminum slope are plotted along the abscissa.
Figure 2:
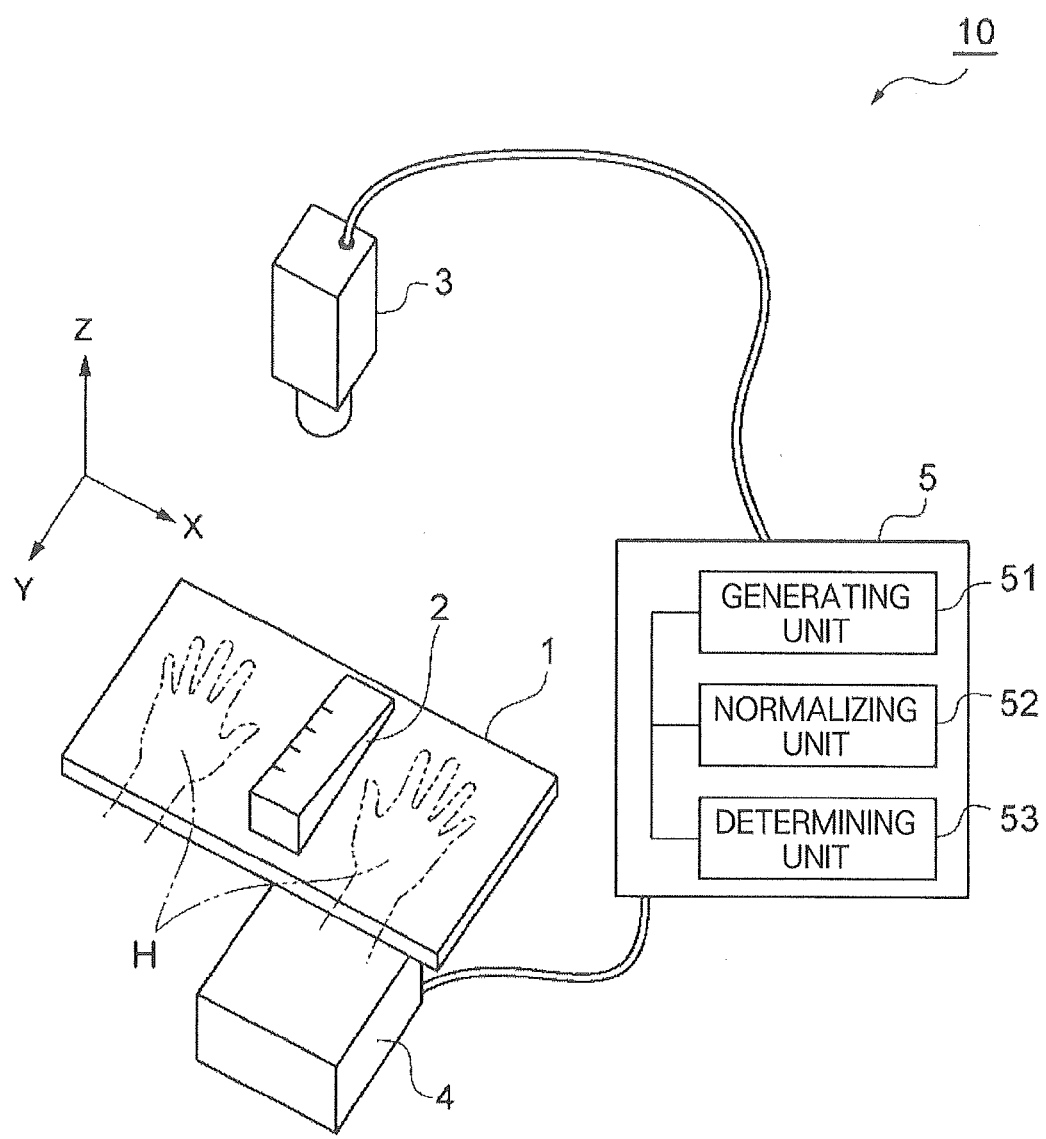
FIG. 2 is a perspective view showing the appearance of one embodiment of a bone density measuring device of the invention.

Now, one embodiment of a bone density measuring device of the invention is described with reference to the appended drawings. FIG. 2 is a perspective view showing the appearance of a bone density measuring device 10 according to this embodiment. As shown in FIG. 2, the bone density measuring device 10 includes: a cassette 1 (a carrying unit), on which a subject's bone H, which is an object to be measured in the bone density (bone mineral quantity) measurement, is placed; an aluminum slope 2 placed on the upper surface of the cassette 1; an X-ray source 3, which applies an X-ray (radiation) to the subject's bone H and the aluminum slope 2; a radiation detector 4 (a detecting unit), which detects the X-rays transmitted through the subject's bone H and the aluminum slope 2; and an analyzing device 5 (arithmetic processor), which can adjust the tube voltage of the X-ray source 3 depending on the result of detection by the radiation detector 4.

The cassette 1 is a table on which the subject's bone H and the aluminum slope 2 to be exposed to the X-rays can be placed. In order to place the subject's bone H, which is the object to be measured in the bone density (bone mineral quantity) measurement, on the cassette 1, palms of the subject, for example, are placed on the cassette 1. The aluminum slope 2 is placed such that a slope face 22, which will be described later, is exposed on the surface at a predetermined center position on the cassette 1.

The aluminum slope 2 is a sloped reference material with the slope face 22 having a predetermined inclination. With referencing imaged data of the X-rays transmitted through the aluminum slope 2, the analyzing device 5 calculates an equivalent aluminum thickness (in millimeter) corresponding to each luminance value. Details of the shape of the aluminum slope 2 will be described later.

The X-ray source 3 is an X-ray generator for applying X-rays to the subject's bone H and the aluminum slope 2 placed on the cassette 1. The tube voltage of the X-rays applied to the subject's bone H and the aluminum slope 2 can be adjusted by the analyzing device 5.

The radiation detector 4 is a flat panel sensor (solid-state image sensor), which detects luminance values of transmitted X-rays (transmitted radiation) transmitted through the subject's bone H and the aluminum slope 2. The detected luminance values indicating luminances of the transmitted X-rays are sent to the analyzing device 5.

The analyzing device 5 is a computer device for carrying out an operation to measure the bone density of the subject's bone H using a correspondence relationship between the detected luminance values of the transmitted X-rays and the thicknesses of the aluminum slope 2. The analyzing device 5 estimates the bone density of the subject's bone H based on the aluminum thickness corresponding to the same luminance value as each luminance value of the subject's bone H. An indication of the tube voltage of the X-rays applied to the subject's bone H and the aluminum slope 2 is displayed as a displayed tube voltage (a given tube voltage inputted and instructed by the operator) on an operation section, a display area, or the like, of the analyzing device 5. The analyzing device 5 includes a generating unit 51, a normalizing unit 52, and a determining unit 53.

The generating unit 51 is an arithmetic section for performing an operation to generate a luminance profile (density profile) based on the luminance values indicating luminances of the transmitted X-rays detected by the radiation detector 4. The luminance profile is information that defines the correspondence relationship between each thickness of the aluminum slope 2 and a luminance value of the transmitted X-rays detected at the thickness.

It should be noted that the generating unit 51 performs the operation to generate the luminance profile by using an average value of luminances detected at portions having the same thickness of the aluminum slope 2 as the luminance value corresponding to the thickness. Details of the operation using an average value of luminances detected at portions having the same thickness as the luminance value corresponding to the thickness will be described later.

The normalizing unit 52 is an arithmetic section for performing an operation to extract a maximum value and a minimum value of luminance values in the luminance profile generated by the generating unit 51 and to normalize the luminance profile based on the maximum value and the minimum value. The normalizing unit 52 extracts, for example, a luminance value at the portion with the smallest thickness of the aluminum slope 2 as the minimum value, and handles this luminance value as a density (normalized value) of 0. Data where the luminance value at the portion of the aluminum slope 2 with the smallest thickness is not a minimum value is handled as NG data.

Further, the normalizing unit 52 calculates a value obtained by dividing the luminance value at each thickness of the aluminum slope 2 by the maximum value of the luminance values in the luminance profile as a density (normalized value) at each thickness of the aluminum slope 2. As a result, the density (normalized value) at the thickness of the aluminum slope that gives the maximum value of the luminance values in the luminance profile has a value of 1. As a result of this normalization, a normalized profile of densities (normalized values) ranging from 0 to 1 depending on the aluminum thickness is generated. Details of the operation to generate the normalized profile and details of the normalized profile that varies depending on the effective tube voltage will be described later.

The determining unit 53 is an arithmetic section for performing an operation to determine whether or not the density (normalized value) corresponding to each of the different aluminum thicknesses (different positions on the aluminum) in the normalized profile is within a range defined in advance. The range defined in advance is a range defined by the displayed tube voltage and the aluminum thickness in the case where the tube voltage shown as the displayed tube voltage is the same as the effective tube voltage. For example, assuming a case where the displayed tube voltage of the X-ray is 50 kV and the density (normalized value) at an aluminum thickness of 70 mm is about 0.58 point, and further assuming that the range defined in advance by the determining unit 53 for the case where the displayed tube voltage is 50 kV and the aluminum thickness is 70 mm is from 0.5 to 0.6 point. In this case, it is determined that the density (normalized value) corresponding to the aluminum thickness of 70 mm is within the range defined in advance.

If at least one of the luminance values corresponding to the different aluminum thicknesses in the normalized profile is out of the range defined in advance, the determining unit 53 determines that the effective tube voltage is not appropriate relative to the displayed tube voltage (there is a relatively large difference between the effective tube voltage and the displayed tube voltage), and adjusts the tube voltage of the X-ray source 3 to an appropriate tube voltage. Specifically, if a luminance value in the normalized profile is smaller than the range defined in advance, the determining unit 53 increases the tube voltage such that a luminance value within the range defined in advance is provided, or if a luminance value in the normalized profile is greater than the range defined in advance, the determining unit 53 decreases the tube voltage such that a luminance value within the range defined in advance is provided. Details of the operation determine whether or not each luminance value is within the range defined in advance will be described later.

(2) Details of Shape of Aluminum Slope

Figure 3:
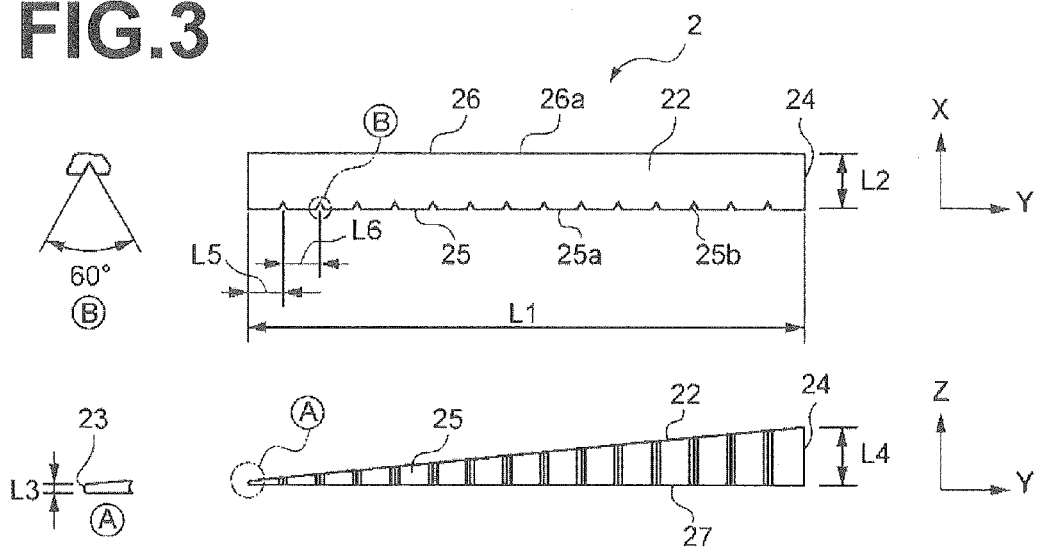
FIG. 3 shows a plan view and a side view for explaining details of the shape of the aluminum slope.

Next, details of the shape of the aluminum slope 2 are described with reference to FIG. 3. FIG. 3 shows a plan view and a side view for explaining the details of the shape of the aluminum slope 2. The aluminum slope 2 is substantially wedge-shaped. Namely, the aluminum slope 2 has a slope face 22, a tip end face 23, a rear end face 24, a reference side face 25, a flat side face 26, and a bottom face 27. The tip end face 23 is connected to the rear end face 24 via the slope face 22, the reference side face 25, the flat side face 26, and the bottom face 27.

A distance L1 from the tip end face 23 to the rear end face 24 is 150 mm, for example. A distance L2 from the reference side face 25 to the flat side face 26 is 15 mm, for example. A height L3 of the aluminum slope 2 at the tip end face 23 is 0.7 mm, for example. A height L4 of the aluminum slope 2 at the rear end face 24 is 15.4 mm, for example.

The slope face 22 is inclined such that the thickness increases along the +Y-direction (the longitudinal direction from the tip end face 23 toward the rear end face 24). For example, the inclination is such that an advancement of 10 mm in the Y-direction results in an advancement of 1 mm in the Z-direction. That is, the inclination is such that the ratio between the length in the Y-direction and the maximum thickness in the Z-direction is 10:1.

The reference side face 25 has a ridge line 25a and a plurality of reference grooves 25b. The reference grooves 25b are provided to extend from the slope face 22 to the bottom face 27 along the Z-direction with being spaced from each other along the Y-direction. The first reference groove 25b is provided at a position apart from the tip end face 23 by a distance L5 in the Y-direction, where the distance L5 is 10 mm, for example. The next reference groove 25b is provided at a position 10 mm apart from the first reference groove 25b in the Y-direction. That is, an interval L6 between the adjacent reference grooves 25b is 10 mm.

In this embodiment, 14 reference grooves 25b are formed along the Y-direction. Each reference groove 25b has a substantially triangular cross section in the X-Y plane. The angle of the apex of the substantially triangular cross section of the reference groove 25b is about 60°, for example.

The flat side face 26 has a ridge line 26a and is located on the opposite side from the reference side face 25. The flat side face 26 is not provided with the reference grooves 25b. The bottom face 27 is formed to be perpendicular to the tip end face 23. Also, the bottom face 27 is formed to be perpendicular to the rear end face 24.

It should be noted that, although the aluminum slope 2 having the slope face 22, as described above, is used as the reference material in this embodiment, the reference material is not limited to one with the thickness increased at a constant rate along the Y-direction. The reference material may have any shape as long as the thickness is varied depending on the position along the Y-direction. For example, a reference material with the thickness varied stepwise along the Y-direction may be used.

Figure 4:
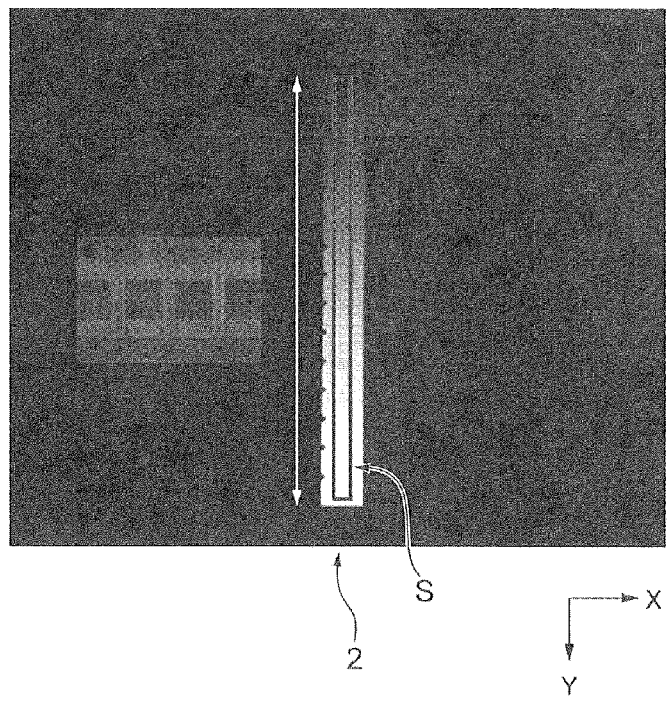
FIG. 4 shows an X-ray image obtained by detecting X-rays transmitted through the aluminum slope.

(3) Details of Operation Using Average Value of Luminances as Luminance Value Next, details of the operation using an average value of luminances as the luminance value is described with reference to FIG. 4. FIG. 4 shows an X-ray image obtained by detecting X-rays transmitted through the aluminum slope 2 placed on the cassette 1. To this X-ray image, an arrow showing the longitudinal direction (Y-direction) of the aluminum slope 2, and a detection range S of the luminance values are added.

The ranges in the horizontal direction and the vertical direction of the detection range S shown in FIG. 4 are fixed. The detection of the aluminum is achieved using a Hough transform-based straight line detection. In this X-ray image, a lighter region is a region with a higher luminance value. A region with a higher luminance value indicates a larger thickness of the aluminum slope 2, for example. A darker region is a region with a lower luminance value. A region with a lower luminance value indicates a smaller thickness of the aluminum slope 2, for example.

The generating unit 51 performs the operation to generate a luminance profile by using an average value of luminances detected at each thickness (in the X direction perpendicular to the Y-direction) of the aluminum slope 2 as the luminance value corresponding to the thickness.

(4) Details of Operation to Generate Normalized Profile

Figure 5:
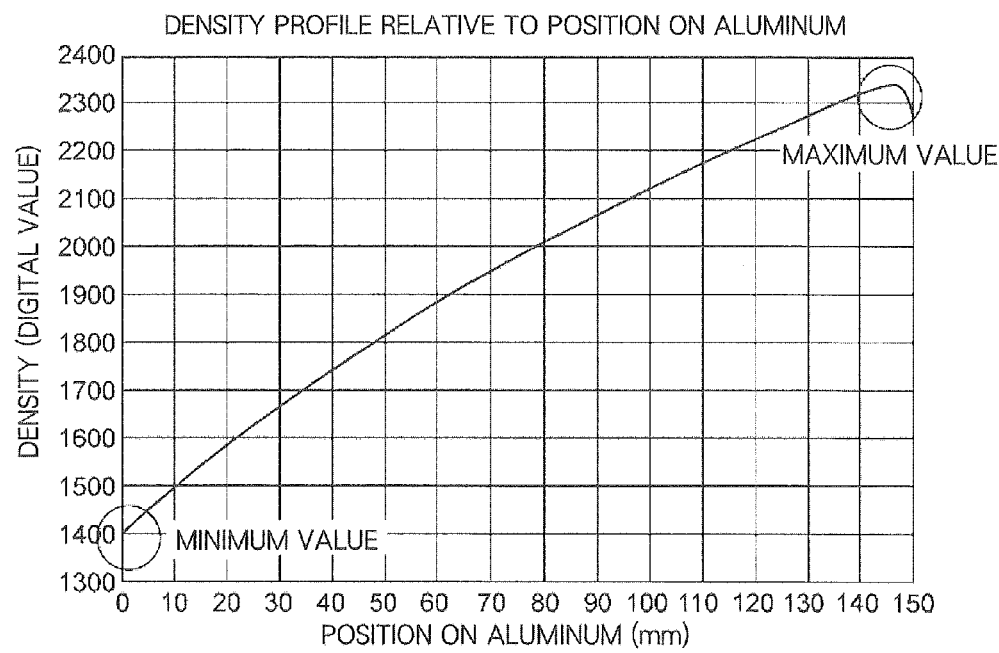
FIG. 5 is a graph of a luminance profile obtained by detecting X-rays transmitted through the aluminum slope.
Figure 6:
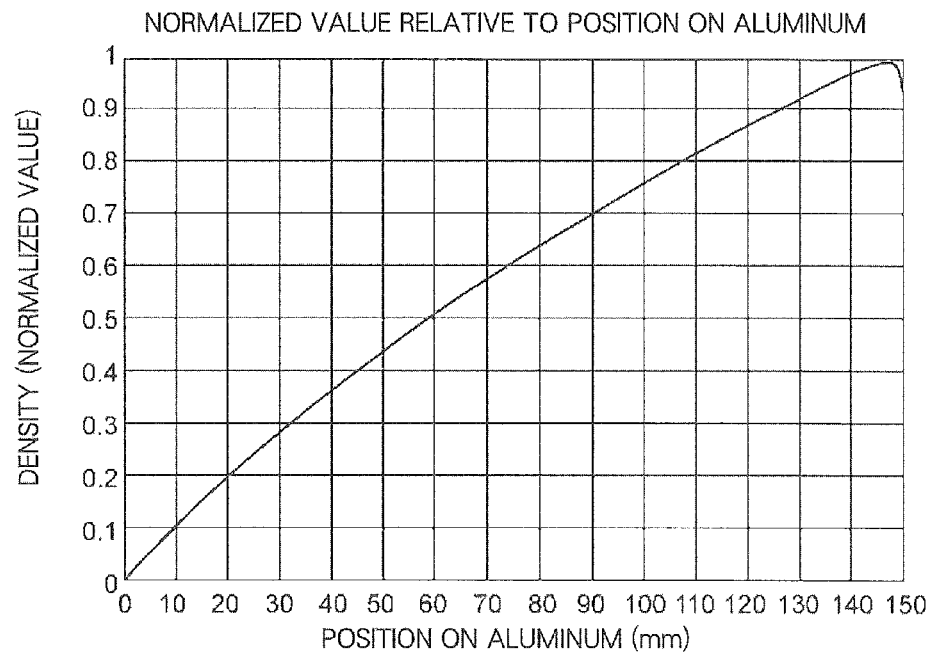
FIG. 6 is a graph of a normalized profile obtained by normalizing the graph shown in FIG. 5.

Next, details of the operation to generate a normalized profile is described with reference to FIGS. 5 and 6. FIG. 5 is a graph of a luminance profile showing changes of the density (the digital value of the luminance value) relative to the thickness of the aluminum slope 2 (the position on the aluminum), which is obtained by detecting X-rays (with the displayed tube voltage being 50 kV) transmitted through the aluminum slope 2 placed on the cassette 1. FIG. 6 is a graph of a normalized profile obtained by normalizing the graph shown in FIG. 5. The density values (digital values of the luminance values) are values obtained by inverting intensities of the X-rays transmitted through the aluminum slope.

The normalizing unit 52 performs the operation to normalize the luminance profile based on the maximum value and the minimum value of the digital values (density values) of the luminance values in the luminance profile shown in FIG. 5. The normalizing unit 52 handles the luminance value (of about 1400 point) at the portion with the smallest thickness of the aluminum slope 2, for example, as the density (normalized value) of 0 point. Further, the normalizing unit 52 calculates the density (normalized value) at each thickness of the aluminum slope 2 based on equation (1) below:

Density (normalized value) at each thickness=(Luminance value at each thickness−Minimum luminance value)/(Maximum luminance value−Minimum luminance value).

As a result, the density (normalized value) at the aluminum thickness that gives the maximum value of the densities (the digital values of the luminance values) in the luminance profile has a value of 1 point. As a result of this normalization, a normalized profile with density values (normalized values) ranging from 0 point to 1 point plotted along the ordinate is generated.

Figure 7:
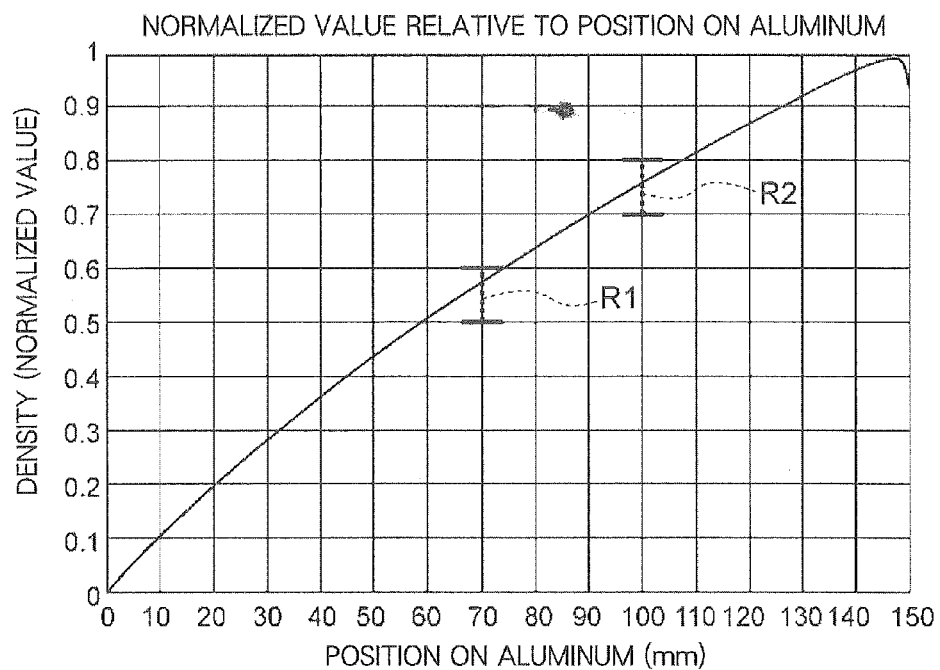
FIG. 7 is a graph where ranges defined in advance are added to the graph of the normalized profile shown in FIG. 6.

(5) Details of Operation to Determine Whether or not Each Luminance Value is within Range Defined in Advance Next, details of the operation to determine whether or not each luminance value is within a range defined in advance are described with reference to FIG. 7. FIG. 7 is a graph where ranges R1 and R2 defined in advance, as described above, are added to the graph of the normalized profile shown in FIG. 6.

It is assumed here that thicknesses of 70 mm and 100 mm, for example, are selected in advance as different aluminum thicknesses of the aluminum slope by the determining unit 53, and the displayed tube voltage of the X-ray is 50 kV, for example. It should be noted that all the different aluminum thicknesses in the normalized profile are preferably within the range from 30 mm to 130 mm. It is also assumed here that, in the normalized profile obtained by the normalizing unit 52, the density (normalized value) corresponding to 70 mm is about 0.58 point and the density (normalized value) corresponding to 100 mm is about 0.76 point, as shown in FIG. 7.

The determining unit 53 stores in advance range information, which indicates, for example, that, in a case where the effective tube voltage is around 50 kV (not greater than 50 kV plus several kV, and not smaller than 50 kV minus several kV), the density (normalized value) at a position where the thickness of aluminum is 70 mm is within the range R1 from 0.5 to 0.6 point, and the density (normalized value) at a position where the aluminum thickness is 100 mm is within the range R2 from 0.7 to 0.8 point.

Then, the determining unit 53 determines that the density (normalized value) of 0.58 point corresponding to 70 mm is within the range R1 from 0.5 to 0.6 point, and the density (normalized value) of 0.76 point corresponding to 100 mm is within the range R2 from 0.7 to 0.8 point. Since these densities (normalized values) are within the ranges R1 and R2 defined in advance, respectively, the determining unit 53 determines that the effective tube voltage is appropriate relative to the displayed tube voltage (the difference between the effective tube voltage and the displayed tube voltage is relatively small).

It should be noted that, in a case where the density (normalized value) corresponding to 70 mm is less than 0.5 point (or greater than 0.6 point), or the density (normalized value) corresponding to 100 mm is less than 0.7 point (or greater than 0.8 point), these densities (normalized values) are out of the ranges defined in advance, respectively, and therefore the determining unit 53 determines that the effective tube voltage is not appropriate relative to the displayed tube voltage (the difference between the effective tube voltage and the displayed tube voltage is relatively large).

Figure 8:
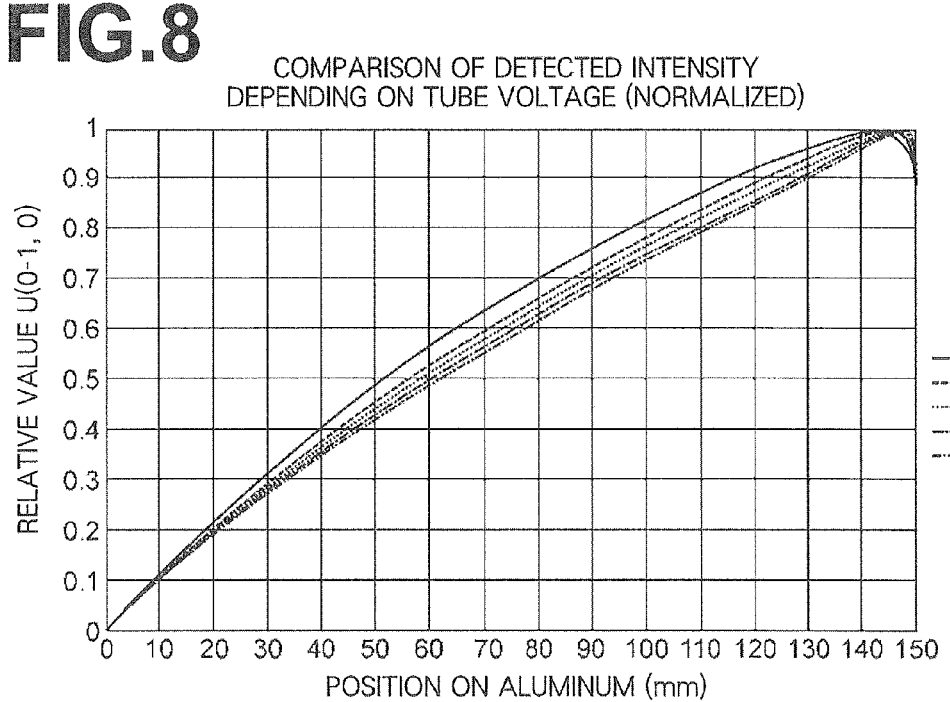
FIG. 8 is a graph of different normalized profiles for five different effective tube voltages.

(6) Details of Normalized Profile that Varies Depending on Effective Tube Voltage Next, details of the normalized profile that varies depending on the effective tube voltage are described with reference to FIG. 8. FIG. 8 is a graph of different normalized profiles for five different effective tube voltages of 40, 46, 50, 55, and 60 kV. Values plotted along the ordinate are relative values as the densities (normalized values) ranging from 0 point to 1 point, and values plotted along the abscissa are thicknesses of the aluminum slope (positions on the aluminum). The determining unit 53 may store in advance the above-described range information for each effective tube voltage determined based on the graph shown in FIG. 8.

(7) Bone Density Measuring Method Performed by Bone Density Measuring Device

Next, a bone density measuring method performed by the bone density measuring device 10 is described with reference to FIG. 9. FIG. 9 is a flow chart for explaining key steps of the bone density measuring method performed by the bone density measuring device 10.

First, as the subject's bone H and the aluminum slope 2 are placed on the cassette 1, the X-ray source 3 applies X-rays to the subject's bone H and the aluminum slope 2 (step S01). Then, the radiation detector 4 detects luminance values of transmitted X-rays transmitted through the subject's bone H and the aluminum slope 2 (step S02).

Subsequently, the generating unit 51 performs the operation to generate a luminance profile based on the luminance values indicating luminances of the transmitted X-rays detected by the radiation detector 4 (step S03). Then, the normalizing unit 52 performs the operation to generate a normalized profile by normalizing the luminance profile based on the maximum value and the minimum value of the digital values (densities) of the luminance values in the luminance profile generated by the generating unit 51 (step S04).

Subsequently, the determining unit 53 performs the operation to determine whether or not each of the densities (normalized values) corresponding to different aluminum thicknesses in the normalized profile is within the range defined in advance (step S05).

If each of the densities (normalized values) is within the range defined in advance, it is determined that the effective tube voltage is appropriate relative to the displayed tube voltage (the difference between the effective tube voltage and the displayed tube voltage is relatively small), and the series of operations ends.

On the other hand, if each of the densities (normalized values) is out of the range defined in advance, it is determined that the effective tube voltage is not appropriate relative to the displayed tube voltage (the difference between the effective tube voltage and the displayed tube voltage is relatively large), and the operation proceeds to step S06.

In step S06, the determining unit 53 adjusts the tube voltage of the X-ray source 3 to an appropriate tube voltage so that the difference between the effective tube voltage and the displayed tube voltage becomes smaller, and the displayed tube voltage is changed along with the adjustment. Then, the series of operations ends once, and the operation proceeds to step S01. In this manner, the series of operations is repeated until the effective tube voltage becomes appropriate relative to the displayed tube voltage.

(8) Operation and Effect of the Invention

According to the analyzing device 5, first, a luminance profile is generated based on luminance values obtained by applying X-rays to the aluminum slope 2, and then a normalized profile is generated based on the maximum value and the minimum value in the luminance profile. Then, whether or not each of the densities (normalized values) corresponding to different aluminum thicknesses in the normalized profile is within the range that is defined by the displayed tube voltage and the aluminum thickness in the case where the tube voltage shown as the displayed tube voltage is the same as the effective tube voltage is determined.

As described above, in place of using a tube voltmeter, luminance values obtained by applying X-rays to the aluminum slope 2 are used to determine whether or not each luminance value corresponding to the tube voltage (effective tube voltage) of the actually applied X-rays is within a range defined in advance corresponding to a desired tube voltage (displayed tube voltage) set by the operator. As a result, whether or not the tube voltage of the actually applied X-rays is appropriate relative to the desired tube voltage can be evaluated without using a tube voltmeter.

Further, according to the bone density measuring device 10 including the analyzing device 5, X-rays transmitted through the subject's bone H and the aluminum slope 2 can be detected with placing the subject's bone H, which is exposed to X-rays with the displayed tube voltage, on the cassette 1.

Further, in the case where the different aluminum thicknesses in the normalized profile are within the range from 30 mm to 130 mm, difference of the relative values (densities) due to difference of the effective tube voltage can more clearly be understood, as shown in FIG. 8. This allows more accurately determining whether or not the effective tube voltage is appropriate relative to the displayed tube voltage (50 kV, for example) (a state where the difference therebetween is relatively small).

Further, the luminance profile is generated using an average value of luminances at portions having the same thickness of the aluminum slope 2 as the luminance value corresponding to the thickness. By using an average value of luminances at portions having the same thickness of the aluminum slope 2 as the luminance value corresponding to the thickness, a more accurate luminance profile can be generated.

(9) Modification

The invention is not limited to the above-described embodiment, and various modifications may be made to the invention. Although the configuration where the radiation detector 4 and the analyzing device 5 are connected via a wired connection so as to be able to communicate with each other, as shown in FIG. 2, is shown as an example in the above-described embodiment, an imaging plate may be used as the radiation detector 4, and a reading device (not shown) that can read luminance values detected by the imaging plate may be connected to the analyzing device 5 via a wired connection without connecting the imaging plate to the analyzing device 5 via a wired connection. Still alternatively, a flat panel detector may be used as the radiation detector 4. Further, although X-ray is used as the radiation in the above-described embodiment, radiation other than X-ray may be used.

INDUSTRIAL APPLICABILITY

According to the present invention, whether or not a tube voltage of actually applied X-rays is appropriate relative to a desired tube voltage can be evaluated without using a tube voltmeter.

What is claimed is:

1. An arithmetic processor for measuring bone density using a correspondence relationship between a luminance value of transmitted radiation and a thickness of a reference material, the luminance value being obtained by applying radiation, which is emitted from a radiation source upon application of a tube voltage to the radiation source, to the reference material having different thicknesses and detecting the radiation transmitted through the reference material, the arithmetic processor comprising:
   a generating unit that performs an operation to generate, based on the detected luminance value, a luminance profile representing the correspondence relationship;
   a normalizing unit that performs an operation to generate a normalized profile by normalizing the luminance profile based on a maximum value and a minimum value in the generated luminance profile; and
   a determining unit that performs an operation to determine whether or not each luminance value corresponding to each of the different thicknesses in the normalized profile is within a range defined in advance by the tube voltage and each thickness.

2. A bone density measuring device comprising:
   the arithmetic processor as claimed in claim 1;
   a carrying unit on which a subject's bone to be exposed to the radiation emitted upon application of the tube voltage is placed; and
   a detecting unit that detects radiation transmitted through the subject's bone and the reference material.

3. The bone density measuring device as claimed in claim 2, wherein the different thicknesses in the normalized profile are within the range from 30 mm to 130 mm.

4. The bone density measuring device as claimed in claim 2, wherein the generating unit performs the operation to generate the luminance profile by using an average value of luminances detected for portions having the same thickness of the reference material as the luminance value corresponding to the thickness.

5. The bone density measuring device as claimed in claim 3, wherein the generating unit performs the operation to generate the luminance profile by using an average value of luminances detected for portions having the same thickness of the reference material as the luminance value corresponding to the thickness.

6. The bone density measuring device as claimed in claim 2, wherein, if a luminance value in the normalized profile is smaller than the range defined in advance, the determining unit increases the tube voltage such that a luminance value within the range defined in advance is provided, or if a luminance value in the normalized profile is greater than the range defined in advance, the determining unit decreases the tube voltage such that a luminance value within the range defined in advance is provided.

* * * * *